United States Patent
Lazar et al.

(10) Patent No.: US 11,674,937 B2
(45) Date of Patent: Jun. 13, 2023

(54) METHOD AND APPARATUS FOR ENCODING ODORANTS

(71) Applicant: THE TRUSTEES OF COLUMBIA UNIVERSITY IN THE CITY OF NEW YORK, New York, NY (US)

(72) Inventors: Aurel A. Lazar, New York, NY (US); Tingkai Liu, Suzhou (CN); Chung-Heng Yeh, Kaohsiung (TW)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 153 days.

(21) Appl. No.: 17/121,246

(22) Filed: Dec. 14, 2020

(65) Prior Publication Data
US 2022/0137017 A1 May 5, 2022

Related U.S. Application Data

(60) Provisional application No. 62/947,999, filed on Dec. 13, 2019.

(51) Int. Cl.
*G01N 33/00* (2006.01)
*G16C 60/00* (2019.01)
*G06F 18/22* (2023.01)

(52) U.S. Cl.
CPC ..... *G01N 33/0031* (2013.01); *G01N 33/0001* (2013.01); *G01N 33/0062* (2013.01); *G06F 18/22* (2023.01); *G16C 60/00* (2019.02); *G01N 2033/0068* (2013.01)

(58) Field of Classification Search
CPC ........... G01N 33/0031; G01N 33/0001; G01N 33/0062; G01N 2033/0068; G06F 18/22
USPC ....................................................... 73/23.34
See application file for complete search history.

(56) References Cited

U.S. PATENT DOCUMENTS

| | | | | | |
|---|---|---|---|---|---|
| 4,638,443 | A | * | 1/1987 | Kaneyasu | G01N 33/0031 340/634 |
| 6,703,241 | B1 | * | 3/2004 | Sunshine | G01N 33/0006 436/2 |
| 2005/0226601 | A1 | * | 10/2005 | Cohen | H04N 21/23614 386/280 |
| 2012/0021932 | A1 | * | 1/2012 | Mershin | G01N 33/0031 422/69 |
| 2020/0213146 | A1 | * | 7/2020 | Kodam | H04L 12/2829 |

OTHER PUBLICATIONS

Beierholm et al., "Comparing Bayesian Models for Multisensory Cue Combination without Mandatory Integration," Advances in Neural Information Processing Systems 20, (2008) 8 pages.

(Continued)

*Primary Examiner* — Nathaniel T Woodward
(74) *Attorney, Agent, or Firm* — Baker Botts L.L.P.

(57) ABSTRACT

The present disclosure provides, method, a system, and apparatus for identifying odorants. For example, the apparatus performs sensing an odorant using an olfactory sensor, encoding the sensed odorant to an electrical signal using an input processor, determining an identity representation of the odorant based on the encoded electrical signal, and determining odorant information using a time-dependent hash code based on the identity representation of the odorant.

18 Claims, 14 Drawing Sheets
(9 of 14 Drawing Sheet(s) Filed in Color)

(56) References Cited

OTHER PUBLICATIONS

Bulkin et al., "Seeing sounds: Visual and auditory interactions in the brain," Current Opinion in Neurobiology, 16:415-419 (2006).
Driver et al., "Multisensory Interplay Reveals Crossmodal Influences on 'Sensory-Specific' Brain Regions, Natural Responses, and Judgments," Neuron, 57:11-23 (2008).
Frye, "Multisensory systems integration for high-performance motor control in flies," Current Opinion in Neurobiology, 20(3):347-352 (2010).
Ghazanfar et al., "Is neocortex essentially multisensory?" Trends in Cognitive Sciences, 10(6):278-285 (Jun. 2006).
Huston et al., "Studying sensorimotor integration in insects," Current Opinion in Neurobiology, 21:527-534 (2011).
Kadunce et al., "The influence of visual and auditory receptive field organization on multisensory integration in the superior colliculus," Experimental Brain Research, 139:303-310 (2001).
Kayser et al., "Multisensory interactions in primate auditory cortex: fMRI and electrophysiology," Hearing Research, 258:80-88 (2009).
Kayser et al., "Visual enhancement of the information representation in auditory cortex," Current Biology 20:19-24 (2010).
Kim et al., "Chapter 11: Recovery of Stimuli Encoded with a Hodgkin-Huxley Neuron using Conditional PRCs," In N.W. Schultheiss, A.A. Prinz, and R.J. Butera, editors, Phase Response Curves in Neuroscience. Springer, 2012 pp. 257-277.
Kording et al., "Causal inference in sensorimotor integration," Advances in Neural Information Processing Systems 19 (2007) 8 pages.
Laurienti et al., "On the use of superadditivity as a metric for characterizing multisensory integration in functional neuroimaging studies," Experimental Brain Research, 166:289-297 (2005).
Lazar et al., "Channel Identification Machines," Computational Intelligence and Neuroscience, 20 pages. (2012).
Lazar et al., "Encoding natural scenes with neural circuits with random thresholds," Vision Research 50:2200-2212 (2010).
Lazar et al., "Faithful Representation of Stimuli with a Population of Integrate-and-Fire Neurons," Neural Computation, 20(11):2715-2744 (2008).
Lazar et al., "Functional Identification of Spike-Processing Neural Circuits," Neural Computation, in press, 2013.
Lazar et al., "Perfect Recovery and Sensitivity Analysis of Time Encoded Bandlimited Signals," IEEE Transactions on Circuits and Systems-I: Regular Papers, 51(10):2060-2073 (2004).
Lazar et al., "Reconstruction of Sensory Stimuli Encoded with Integrate-and-Fire Neurons with Random Thresholds," EURASIP Journal on Advances in Signal Processing, 2009, 14 pages.
Lazar, "Population Encoding with Hodgkin-Huxley Neurons," IEEE Transactions on Information Theory, 56(2) (2010) 34 pages.
Lazar, "Time Encoding with an Integrate-and-Fire Neuron with a Refractory Period," Neurocomputing, 58-60:53-58 (2004).
Ma et al., "Linking neurons to behavior in multisensory perception: A computational review," Brain Research, 1242:4-12 (2008).
Stein et al., "Multisensory integration: Current issues from the perspective of a single neuron," Nature Reviews Neuroscience, 9:255-266 (2008).
Yeh, "Mechanistic Models of Neural Computation in the Fruit Fly Brain," Columbia University, Electrical Engineering Thesis (Oct. 28, 2019).
Yevgeniy B. Slutskiy. Identification of Dendritic Processing in Spiking Neural Circuits. PhD thesis, Columbia University, 2013.

\* cited by examiner

METHOD AND APPARATUS FOR ENCODING ODORANTS

CROSS-REFERENCE TO RELATED APPLICATION

This application claims priority to U.S. Provisional Patent Application No. 62/947,999, filed Dec. 13, 2019, the contents of which are incorporated by reference herein in its entirety.

STATEMENT REGARDING FEDERALLY SPONSORED RESEARCH

This invention was made with government support under grant number 1544383 awarded by the National Science Foundation (NSF), and grant number FA9550-16-1-0410 awarded by Air Force Office of Scientific Research (AFOSR). The government has certain rights in the invention.

BACKGROUND

Certain organisms, whether human or non-human, have an ability to sense odorants. An odorant can be a chemical or substance that has a distinctive smell.

While certain organisms are capable of sensing odorants using their olfactory systems, a need exists for a robust method or apparatus that can process, identify, and/or classify odorants.

SUMMARY

The disclosed subject matter provides an odorant encoding machine (OEM) for detecting or sensing an odorant. In certain embodiments, the OEM includes one or more circuit layers including one or more processors, a memory storing instructions, which when executed by the one or more processors, cause the apparatus to perform sensing an odorant using an olfactory sensor, encoding the sensed odorant to an electrical signal using an input processor, determining an identity representation of the odorant based on the encoded electrical signal, and determining odorant information using a time-dependent hash code based on the identity representation of the odorant.

In certain embodiments, the determining of the odorant information includes evaluating a distance between the identify representation of the electrical signal representing the odorant; and comparing the distance to other distances, where the other distances represent a pair of previously identified odorants stored in the memory. In certain embodiments, the distance is an absolute distance. The odorant can be a monomolecular odorant or an odorant mixture.

In certain embodiments, the processors can additionally classify the odorant information of a monomolecular odorant or an odorant mixture.

In certain embodiments, the identity of the odorant and the concentration waveform of the odorant are combined as a combinatorial code of multidimensional spoke trains.

In certain embodiments, the encoding includes determining at least one of an identity of the odorant or a concentration waveform of the odorant.

In certain embodiments, the identity representation is a concentration-invariant representation of the odorant.

In certain embodiments, the OEM further includes a display. In certain embodiments, the processors can additionally display an indication of the odorant information.

In certain embodiments, the one or more circuit layers include a first circuit layer which performs the encoding the sensed odorant to an electrical signal, a second circuit layer which performs the determining an identity representation of the odorant based on the encoded electrical signal, and a third circuit layer which performs determining odorant information using a time-dependent hash code based on the identity representation of the odorant. In certain embodiments, the first circuit layer includes an olfactory sensor array. In certain embodiments, the sensors of the olfactory sensor array include asynchronous samplers. In certain embodiments, the on-off circuit includes at least one of a low pass-filter or a high pass filter. In certain embodiments, the predictive coding circuit is configured to at least one of smooth, pool, and normalize the electrical signal.

In certain non-limiting embodiments, the first circuit layer can include one or more input processors or transducers. The processors or transducers, for example, can be olfactory sensors or an array of olfactory sensors that can convert or encode odorants into an electric signal. In some embodiments, the olfactory sensors can employ non-linear processing to encode at least one of an identity of the odorant and/or a concentration waveform of the odorant into the electric signal. The identity and/or concentration waveform, as well as any other additional information regarding the odorant, can be represented as a combination code of a multidimensional spike train.

In certain non-limiting embodiments, the second circuit layer can include one or more components, such as a processor or filter, to encode the electric signal outputted by the first circuit layer. The components in the second circuit layer, for example, can help to encode the outputted electric signal of the first circuit layer into a concentration-invariant representation that recovers an odorant identity. In some embodiments the concentration-invariant representation can help to reduce the intensity of the odorant from the representation. The second circuit layer can also include an on-off component, which can include one or more filters, to capture the onset and offset of a given odorant stimulus. The captured onset and offset can be used as part of the asynchronous processing for identifying or classifying the time-varying odorant.

In certain embodiments, the third circuit layer, for example, can include a feedback normalization processor that can compute a high dimensional sparse representation of odorant information as a robust time-dependent hash. As such, the third circuit layer can perform as a real-time hashing circuit.

The disclosed subject matter also provides methods for detecting or sensing an odorant. An example method can also include identifying or classifying the sensed odorant based on one or more properties of the odorant. The odorant can be a mono-molecular odorant, an odorant mixture, or any other odorant.

The techniques disclosed herein can help to sense an odorant, such as a mono-molecular odorant or an odorant mixture, and classify or identify the sensed odorant. For example, the first, second, and/or third circuit layer can help to determine the distance between steady-state representation of known pairs of odorants, which can include determining or separating the absolute distance between one or more pairs of odorants. The determined distance can be used to capture or represent the relationship between similar and dissimilar odorants, which can help to determine or render an odorant classification or identity.

In certain non-limiting embodiments, the disclosed techniques can be used to sense, detect, identify, and/or classify mono-molecular odorants and/or odorant mixtures. Using the circuit layers, the apparatus can detect previously unclassified odorants resulting from mixing one or more mono-molecular components or odorants.

BRIEF DESCRIPTION OF THE DRAWINGS

The application file contains at least one drawing executed in color. Copies of this patent with color drawings will be provided by the Office upon request and payment of the necessary fee.

FIG. 10A shows a mixture of two odorant stimuli. FIG. 10B shows output of the predictive circuit. FIG. 10C shows output of the on-off circuit 122. FIG. 10D shows output of the second circuit layer 120. The affinity vector of the two odorants is shown as a heatmap at top right corner.

FIG. 11A shows concentrations of odorants. FIG. 11B shows the second layer index. FIG. 11C shows the third layer index. FIG. 11D shows a percentage of active channels in the third circuit layer 130.

DETAILED DESCRIPTION

The patent or application file contains at least one drawing executed in color. Copies of this patent or patent application publication with color drawing(s) will be provided by the Office upon request and payment of the necessary fee.

The present disclosure generally describes odorant encoding machine (OEM) for detecting or sensing an odorant. The present disclosure further provides methods of detecting or sensing an odorant using said apparatus. The method can also include identifying or classifying the sensed odorant based on one or more properties of the odorant.

Figure 1:
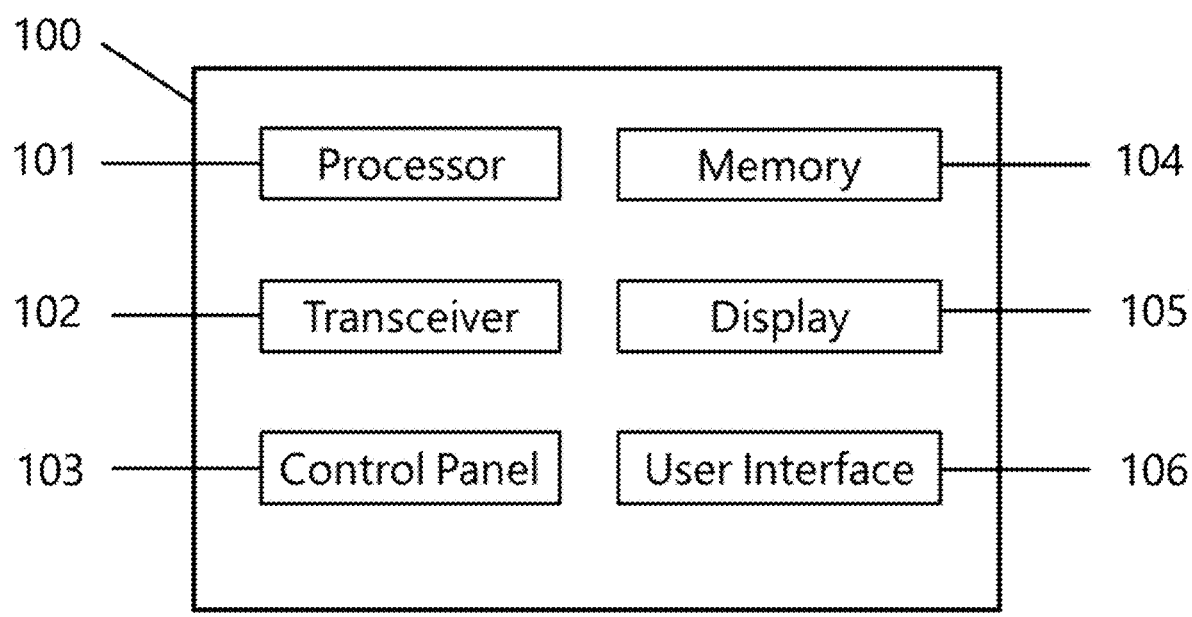
FIG. 1 provides a diagram illustrating exemplary components of a system or apparatus according to some examples of the disclosed subject matter.

FIG. 1 is an example of an apparatus according to some non-limiting embodiments of the disclosed subject matter. In particular, FIG. 1 shows an apparatus 100. In certain embodiments, the apparatus 100 is OEM.

In certain embodiments, the OEM includes at least one processor or control unit 101. At least one memory 104 can also be provided in each OEM. Memory 104 can include computer program instructions or computer code contained therein, which instructions or code can be executed by the processor 101. The OEM can also include networked components communicating over a local network, a wide area network, wirelessly and/or wired, or by any other coupling that allows communication of data from one system component to another system component or another system.

In certain embodiments, one or more transceivers 102 can be provided. The OEM can further include or be connected to display 105, which can display the input or output data.

In certain non-limiting embodiments, at least one memory 104 including computer program code can be configured to, when executed by the at least one processor 101, cause the apparatus to perform any or all of the processes described herein. Processor 101 can be embodied by any computational or data processing device, such as a central processing unit (CPU), digital signal processor (DSP), application specific integrated circuit (ASIC), programmable logic devices (PLDs), field programmable gate arrays (FPGAs), input/output (I/O) circuitry, digitally enhanced circuits, or comparable device, or any combination thereof.

The OEM system 200 can also include a system control panel 103. System control panel 103 can include user interface 106. In certain embodiments, use interface 106 can be a separate piece of hardware that is not located on control panel 103. The use interface 106 can be a touch screen made of glass or any other material known to a person of skill in the art.

For firmware or software, the implementation can include modules or a unit of at least one chip set (for example, including procedures and/or functions). Memory 104 can independently be any suitable storage device, such as a non-transitory computer-readable medium, a hard disk drive (HDD), random access memory (RAM), flash memory, or other suitable memory. The memories can be combined on a single integrated circuit with a processor, or can be separate therefrom.

Furthermore, the computer program instructions can be stored in the memory and be processed by the processors, and can be any suitable form of computer program code, for example, a compiled or interpreted computer program written in any suitable programming language. For example, in certain non-limiting embodiments, a non-transitory computer-readable medium can be encoded with computer instructions or one or more computer programs (such as added or updated software routine, applet or macro) that, when executed in hardware, can perform a process such as one of the processes described herein. Computer programs can be coded by a programming language, which can be a high-level programming language, such as objective-C, C, C++, C#, Java, etc., or a low-level programming language, such as a machine language, or assembler. Alternatively, certain non-limiting embodiments can be performed entirely in hardware.

Figure 2:
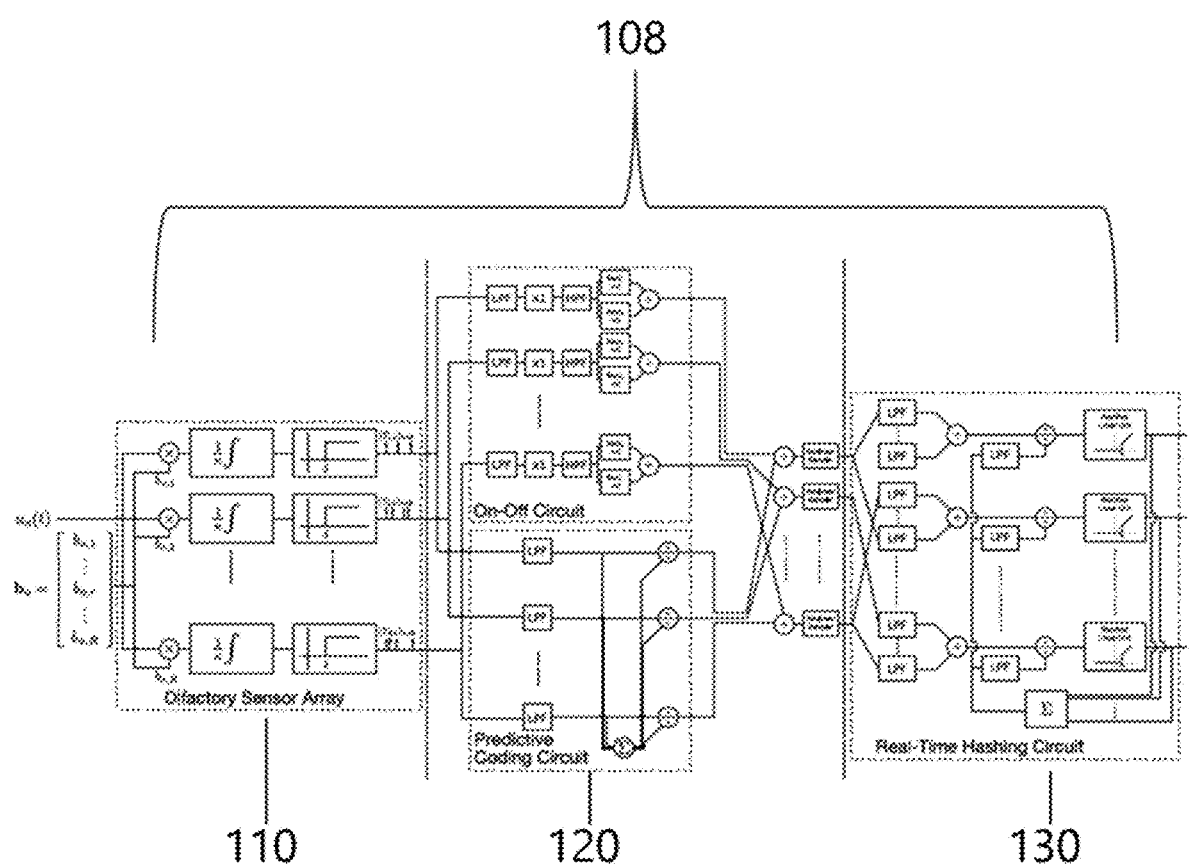
FIG. 2 shows a circuit diagram for an odorant encoding machine according to certain embodiments of the present disclosure having a first circuit layer 110, a second circuit layer 120 and a third circuit layer 130.
Figure 3:
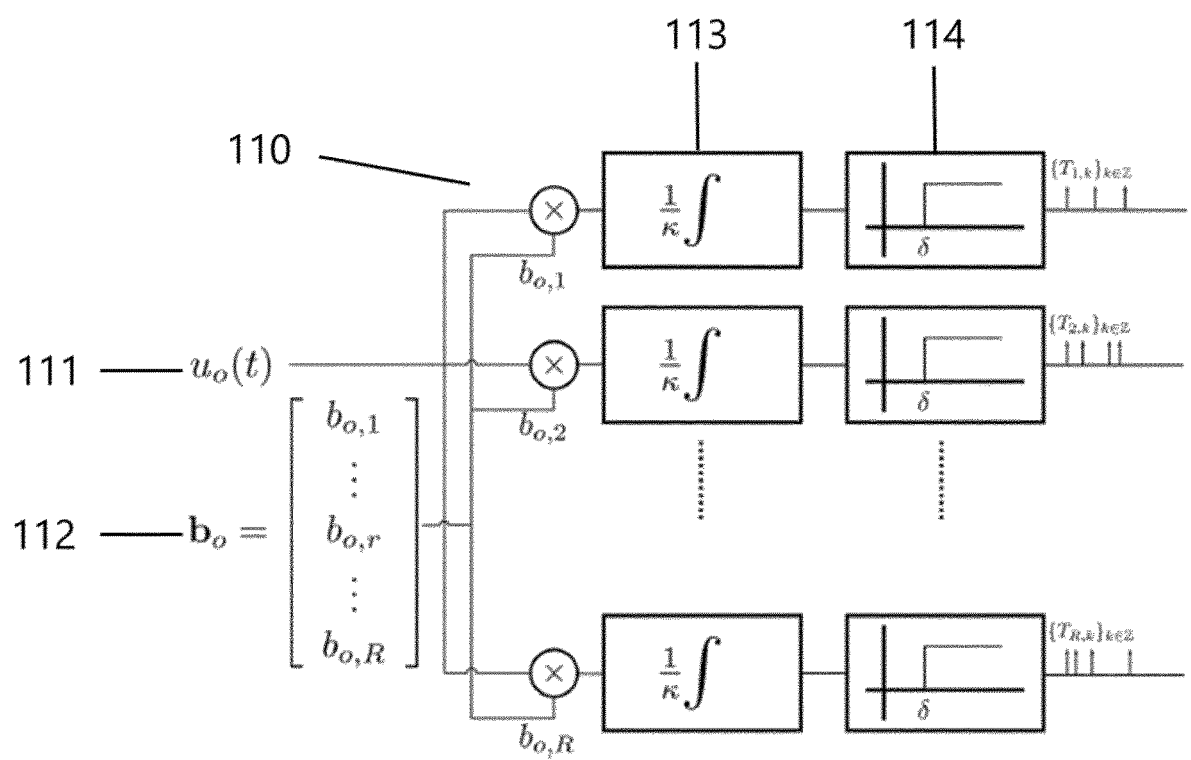
FIG. 3 shows a first circuit layer 110 according to certain embodiments of the present disclosure.
Figure 4:
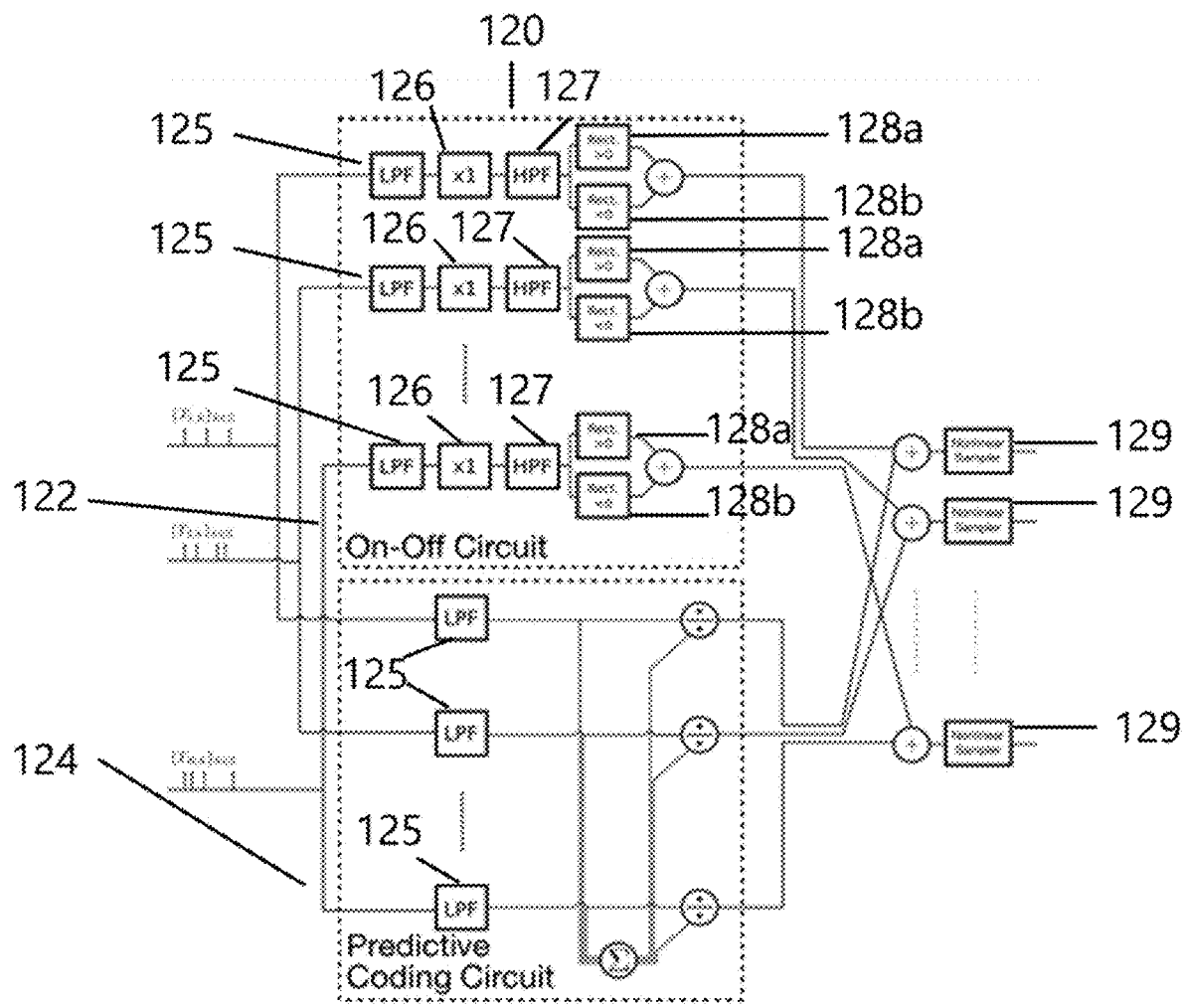
FIG. 4 shows a second circuit layer 120 according to certain embodiments of the present disclosure.
Figure 5:
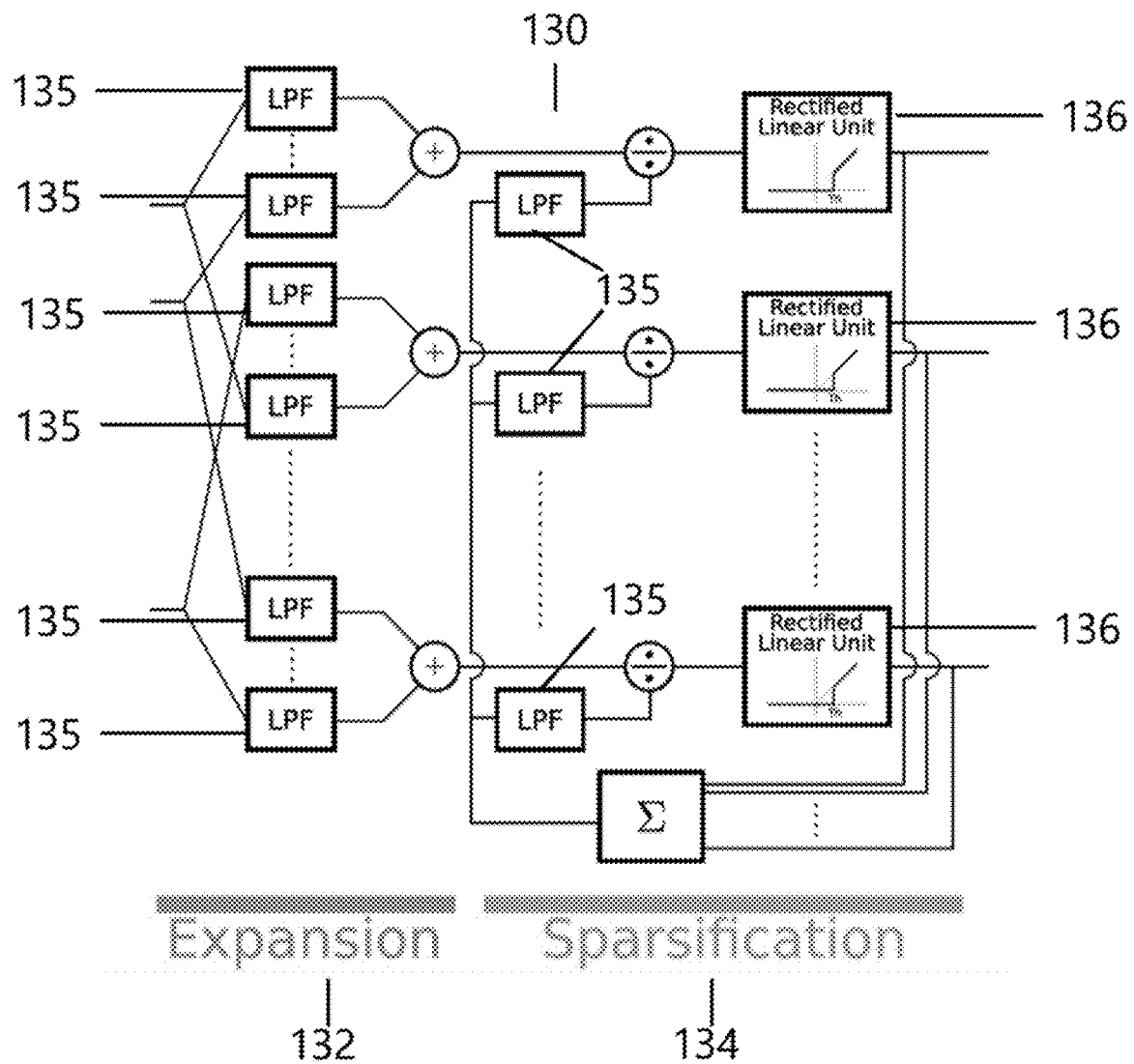
FIG. 5 shows a third circuit layer 130 according to certain embodiments of the present disclosure. In certain embodiments, the third circuit layer 130 can be a real-time hashing circuit (RTHC) developed for generating sparse time-dependent hashing of input odorant identity. In certain embodiment the third circuit layer 130 includes an Expansion sub-circuit 132 and a Sparsification sub-circuit 134.

In certain embodiments, the OEM described herein includes circuitry 108 including three circuit layers as shown in FIG. 2. Particularly, the OEM can include a first circuit layer 110, which can include an olfactory sensor array, a second circuit layer 120, which can include at least one of a predictive coding circuit 124 and on-off circuit 122, and a third circuit layer 130 that can include a real-time hashing circuit. Each of the first circuit layer, the second circuit layer 120 and the third circuit layer 130 is shown in FIGS. 3-5, respectively. Even though the first circuit layer 110, the second circuit layer 120, and the third circuit layer 130 are described to have specific components, a person skilled in the art would readily recognize that each of these one or more components can be included in any combination of the first, second, or third circuit layers.

Figure 6:
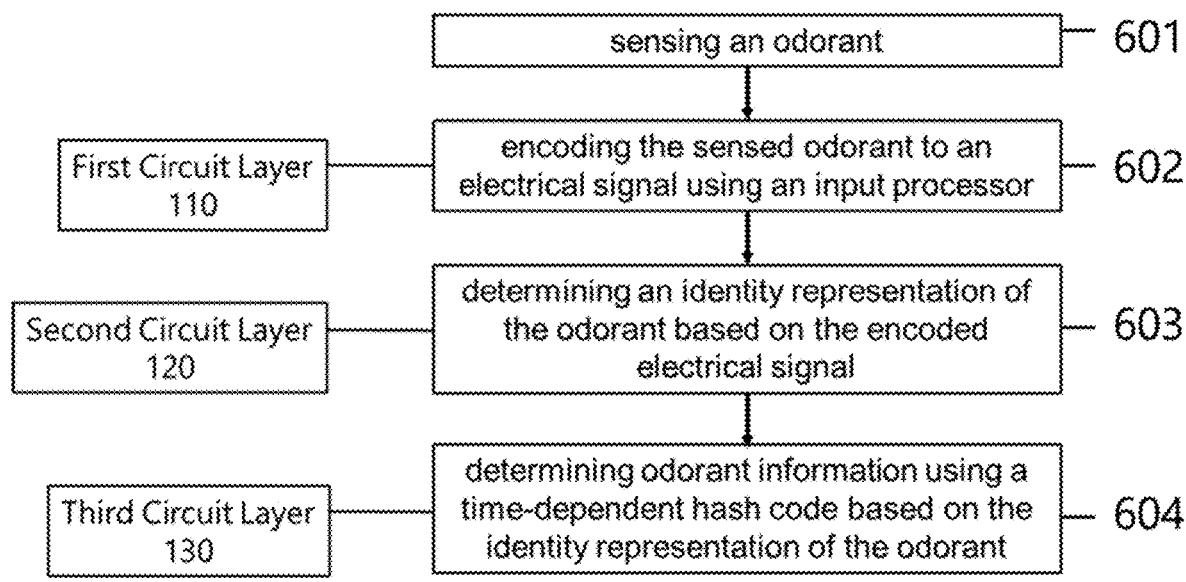
FIG. 6 provides a flow diagram of a method or process according to some examples of the disclosed subject matter.

FIG. 6 illustrates a process for sensing an odorant. In particular, at 602, first circuit layer 110 can be used for encoding the sensed odorant to an electrical signal using an input processor. Then, at 603, the second circuit layer 120 can be used for determining an identity representation of the odorant based on the encoded electrical signal. After this at 604, the third circuit layer 130 can be used for determining odorant information using a time-dependent hash code based on the identity representation of the odorant.

In certain embodiments, the first circuit layer 110 includes one or more input processors of the OEM used to encode the sensed odorant into an electrical signal. In certain embodiments, the olfactory sensors employ nonlinear processing to encode both the odorant identity and the odorant concentration waveform and represent the information about the odorant as a combinatorial code of multidimensional spike trains.

In certain embodiments, the intensity of the odorant can be removed from its representation to allow for robust classification of the odorant identities. In such embodiments, the second circuit layer 120 can be devised to encode the output of the first layer into a concentration-invariant representation that recovers the odorant identity. In certain embodiments, the second circuit layer 120 includes an on-off component, which can capture the onset and offset of a given odorant stimulus. In certain embodiments such configuration enables asynchronous online processing of potentially time-varying odorant identity.

In certain embodiments, the second circuit layer 120 can be used to determine an identity representation of the odorant based on the encoded electrical signal. In certain embodiments, the third circuit layer 130 can act as a feedback normalization processor that computes a high dimensional sparse representation of odorant information as a robust time-dependent hash. In certain embodiments, the third circuit layers 130 can be used to determine odorant information using a time-dependent hash code based on the identity representation of the odorant. Each of the first circuit layer 110, the second circuit layer 120 and the third circuit layer 130 is further described below.

First Circuit Layer 110

Figure 7:
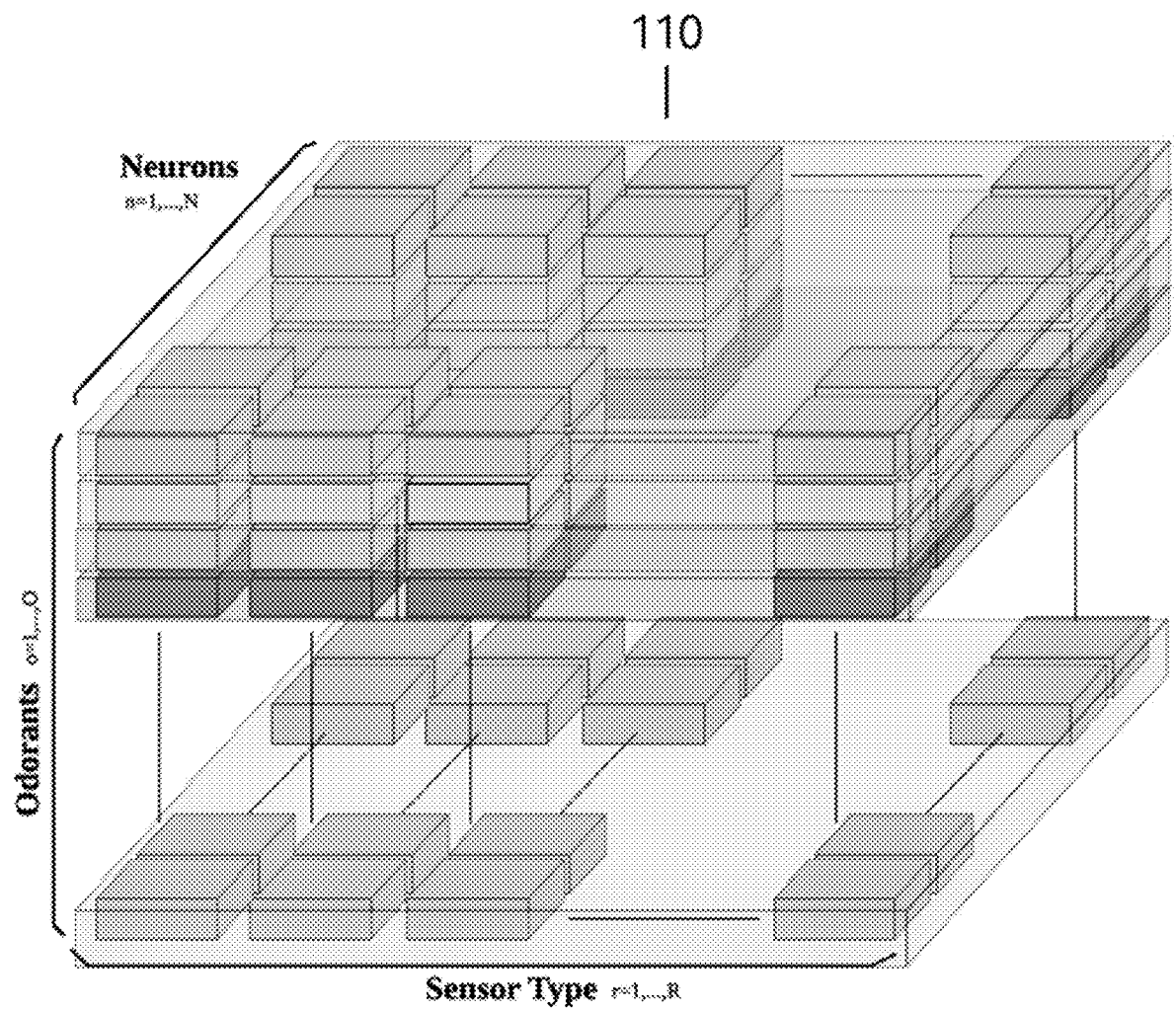
FIG. 7 shows an affinity tensor of the first circuit layer 110 according to certain embodiments of the present disclosure.

In certain embodiments, the odorant can be a monomolecular odorant o with a concentration waveform $u_O(t)$. In such embodiments, the olfactory sensor array associates the odorant o with an affinity tensor $b_o$. Each entry $b_{o,r}$ defines the affinity value between the odorant o and the r-th olfactory sensor. The space of monomolecular odorants can be hence characterized by the space of the affinity tensor b, as illustrated in FIG. 7.

In certain embodiments, the first circuit layer 110 includes an array of olfactory sensors. In certain embodiments, the olfactory sensor array includes an array of asynchronous samplers. Each of the asynchronous samplers represents the odorant information as a spike train $\{T_{i,k}\}k \in \mathbb{Z}$ by sampling the product between the affinity value $b_{o,r}$ and the concentration waveform $u_0(t)$, $$\int_{t_{r,k}}^{t_{r,k+1}} b_{o,r} \cdot u_0(S) ds = k\delta \qquad [1]$$

In certain embodiments, the olfactory sensor array encodes both the affinity vector $b_o$ and the concentration waveform $u_0$ into a multidimensional spike trains $(\{T_{1,k}\}_{k \in \mathbb{Z}}, \ldots, \{T_R,k\}_{k \in \mathbb{Z}}$. The resulting multidimensional spike train is a concentration-dependent combinatorial code for the odorant o. An illustration of the affinity tensor for monomolecular odorants is shown in FIG. 7.

FIG. 3 shows the circuit 110 and its components concentration waveform $u_0(t)$ 111, affinity tensor $b_o$ 112.

Second Circuit Layer 120

In certain embodiments, the second circuit layer 120 of the odorant encoding machine encodes the odorant information into a concentration-invariant combinatorial code that represents at least one of the odorant identity or the timing of the presence of the odorant. In certain embodiments, when both of these two aspects (i.e., identity and timing), are encoded in parallel by the predictive coding circuit 124 and the on-off circuit 122, respectively. The predictive coding circuit 124 and the on-off circuit 122 are further described with reference to the FIG. 4.

In certain embodiments, in the on-off circuit 122, the output of the olfactory sensor array first passes through a bank of low lass filters (LPF) 125 to provide a continuous analog signal. The continuous signal can be then encoded by a nonlinear processor $x_1$ 126, that eliminates infinitesimal fluctuations of odorants and makes the circuit robust against odorant pruning. The output of xi can be encoded by a bank of high pass filters (HPF) 127 followed by positive and negative rectifiers 128a and 128b, respectively. Thereby, the on-off circuit 122 encodes the gradient of the odorant concentration and generates transient responses only at the onset and the offset of the odorant concentration waveform.

In certain embodiments, in the predictive coding circuit 124, the output of the olfactory sensor array generates a concentration-dependent combinatorial code, and the odorant identity and the odorant concentration are indistinguishable in the combinatorial code because of the multiplicative coupling in equation [1]. The predictive coding voids the coupling through three procedures. In certain embodiments, the predictive coding circuit 124 first smoothens the output of olfactory sensor array with a bank of low pass filters. In certain embodiments, the output signals of the filter bank are then pooled together to compute a prediction of the odorant concentration value. In certain embodiments, the predicted concentration value can be used to remove the concentration information by normalizing the output of the filter bank.

In certain embodiments, the output of the on-off circuit 122 and the predictive coding circuit 124 can be summed up and later encoded by a bank of nonlinear samplers 129.

Third Circuit Layer 130

In certain embodiments, the third circuit layer 130 can be a real-time hashing circuit, and represents odorant information as a high dimensional, sparse, real-time hash code. Certain embodiments of the third circuit layer 130 are described further below with reference to FIG. 5.

In certain embodiments, the outputs of nonlinear samplers from the second circuit layer 120 undergoes dimensionality expansion through the Expansion sub-circuit 132. See, left side of FIG. 5. The second circuit layer 120 outputs can be passed through a weighted low pass filter 135 bank before they are linearly combined into a much higher dimensional representation. In certain particular embodiments, the outputs from the second circuit layer 120 are expanded about 20 times. In certain embodiments, the outputs from the second circuit layer 120 are expanded from about 5 time to about 50 times. In certain embodiments, each channel of the third circuit layer 130 receives input from randomly selected subset of all channels of the second circuit layer 120, with randomly sampled weights for each of the low pass filters 135.

Figure 8:
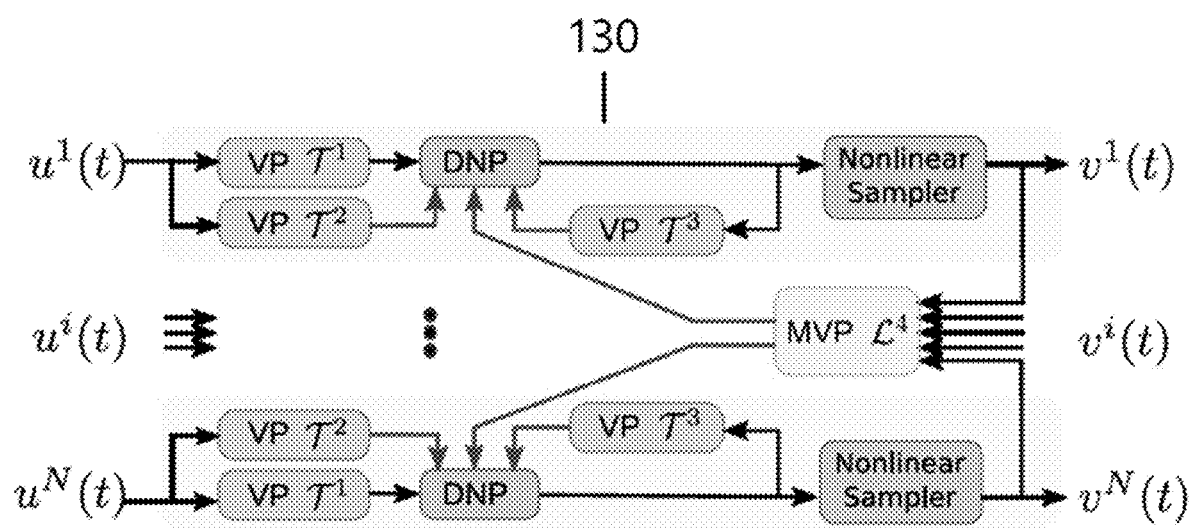
FIG. 8 shows a RTHC of FIG. 5 as a generalized Divisive Normalization Circuit according to certain embodiments.
Figure 9:
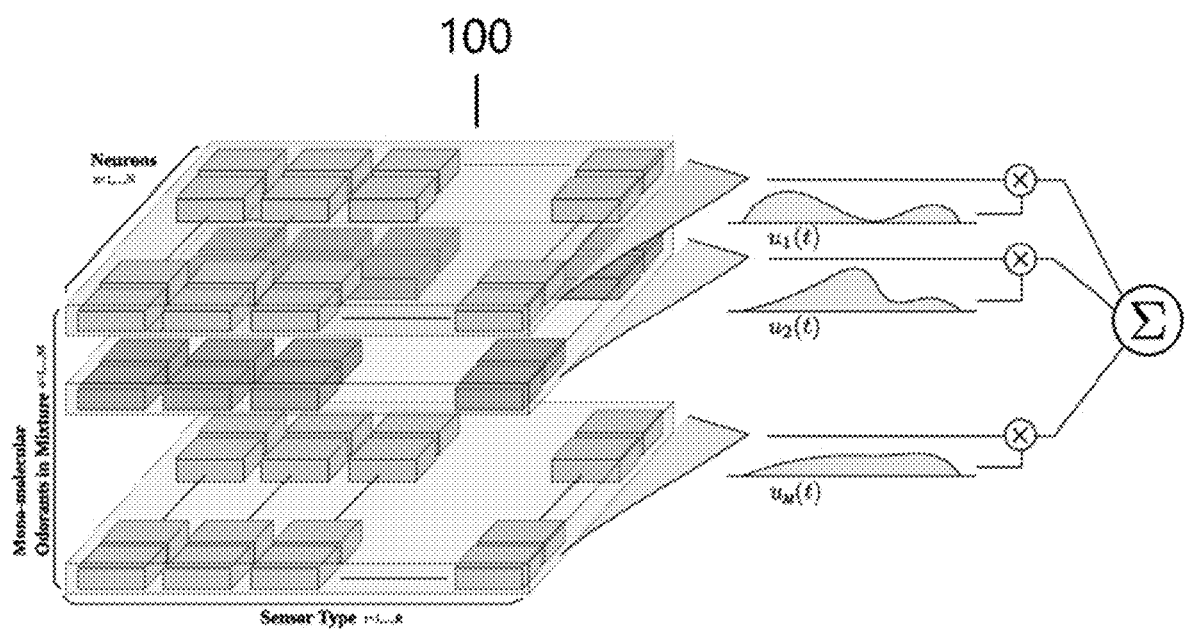
FIG. 9 shows odorant mixture model according to certain embodiments of the present disclosure.

In certain embodiments, the high dimensional representation of the Expansion sub-circuit 132 can be then sparsified by the Sparcification sub-circuit 134. See, right side of FIG. 5. In certain embodiments, the sparsification can be implemented by a Divisive Normalization circuit: each channel can have a first hard threshold implementing using Rectified Linear Units (ReLU) 136 with shared threshold values; the mean value of threshold outputs can be estimated through summation; the summation result can be filtered using a first low pass filter and then used to normalize each channel through a feedback division. In effect, the summation and Low Pass Filters in the Sparsification sub-circuit 134 serve as a leaky integrator of the combined activation of all channels, which approximates mean values of all output streams. The feedback division can then normalize each output channel by their combined mean value, allowing a shared threshold value in the ReLU 136 to extract a fix percentage of output streams with the highest responses. As shown in FIG. 8 the feedback normalization circuit can be a more general class of Divisive Normalization Circuits, thereby allowing alternative implementations with potentially more complex behaviors like variance adaptation.

In certain embodiments, all components of the circuit process time-varying representation are from the upstream of the second circuit layer 120. In these embodiments, the third circuit layer 130 generates a real-time representation of the odorant identity information.

In certain embodiments, the OEM end-to-end can transform input odorants, with combinations of indeterminate number of odorant molecules, into a representation of fixed dimensionality. In certain embodiments, the Hash Code implemented by OEM satisfies a variety of properties desirable for general hashing such as collision resistance.

In certain embodiments, the OEM of the present disclosure can be used to analyze not only mono-molecular (pure) odorants, but also mixtures of odorants. In certain such embodiments, the mixtures can be represented as the linear combination of its mono-molecular components at the input to the olfactory sensory array. In particular, if a mixture of M mono-molecular odorants, each represented as $(b_o, u_o)$ for $o \in O$, where $O:|O|$ M is the set of mono-molecular odorants in the mixtures. In certain embodiments, the mixture's combined input to the sensor array would thus be $\Sigma_{o \in O} b_{o,r} \cdot u_0(t)$ for $r=1, \ldots, R$, where $r$ is represented by the equation [2] below:

$$\int_{t_{r,k}}^{t_{r,k+1}} \Sigma_{o \in O} b_{o,r} \cdot u_0(S) ds = k\delta \qquad [2]$$

Due to the combinatorial nature of odorant mixtures, the space of odorants/mixtures required to be classified and recognized increases exponentially as the complexity of odorant mixtures increases. As the number of channels in the second circuit layer 120 is the same as the number of sensors in the first circuit layer 110, dimensionality expansion can be done in the third circuit layer 130.

EXAMPLES

Event-driven Identity Encoding

Figure 10A:
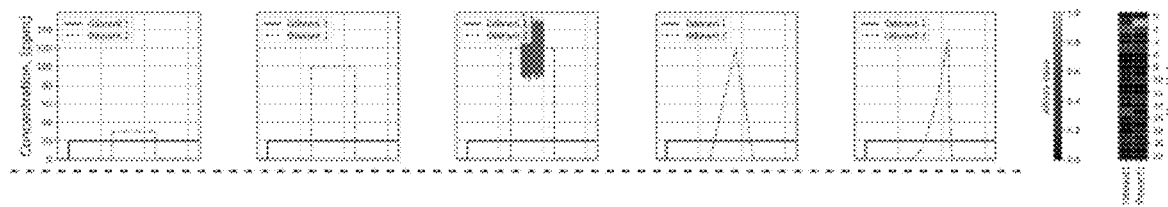
FIGS. 10A-10D show Evaluation of the on-off circuit 122 and the predictive circuit in the second circuit layer 120 according to certain embodiments of the present disclosure.
Figure 10B:
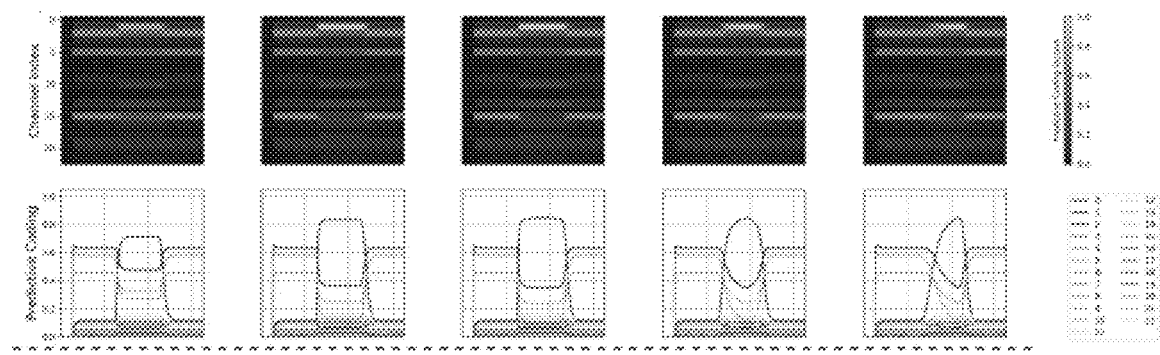
Figure 10C:
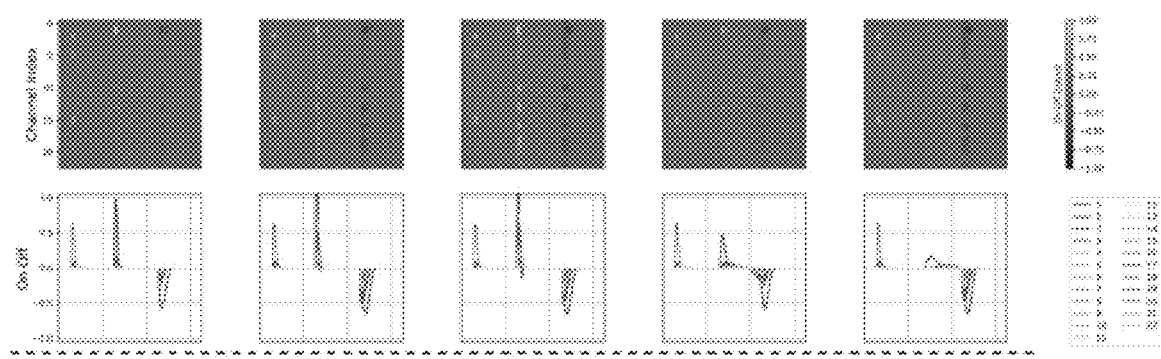
Figure 10D:
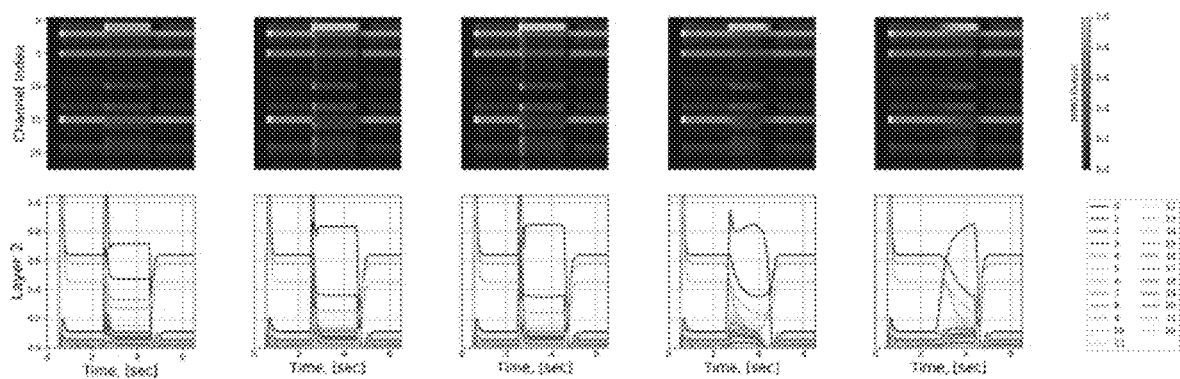
Figure 11A:
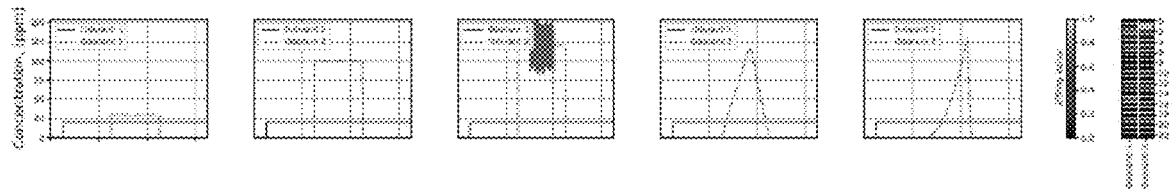
FIGS. 11A-11D show the second circuit layer 120 and the third circuit layer 130 representations for odorant mixtures according to certain embodiments of the present disclosure.
Figure 11B:
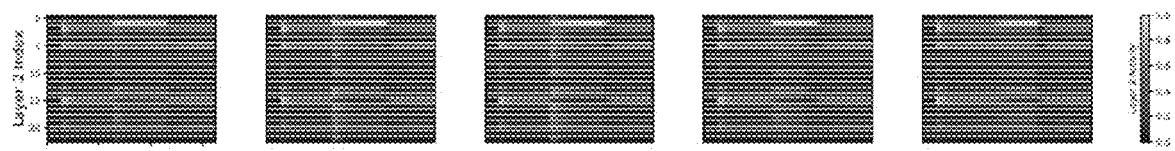
Figure 11C:
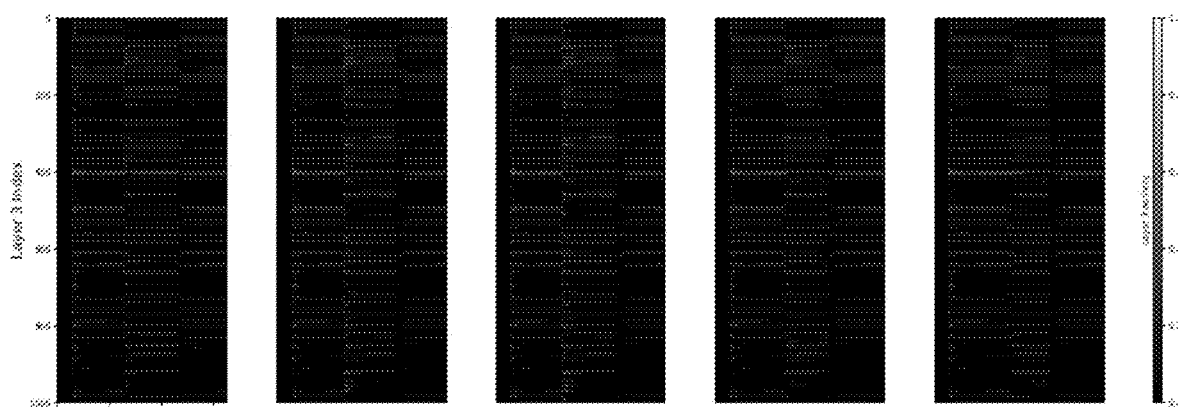
Figure 11D:
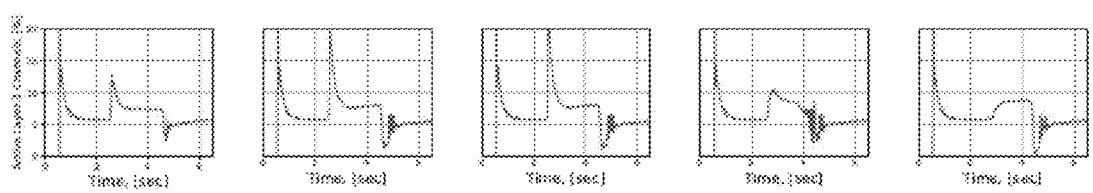
Figure 12A:
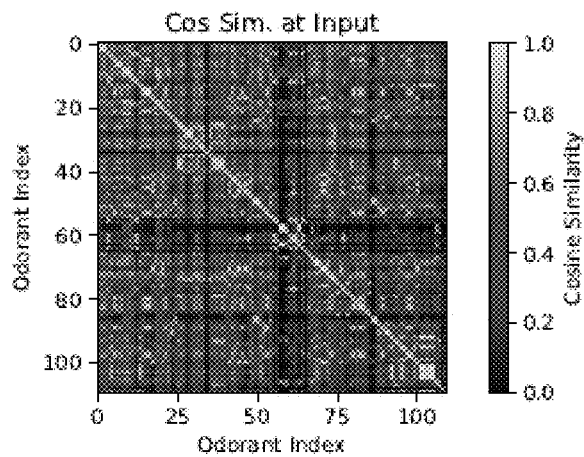
FIGS. 12A-12D show cosine similarity of neural response for every pair of odorants at input of the first circuit layer 110, the second circuit layer 120 and the third circuit layer 130, respectively, according to certain embodiments of the present disclosure.
Figure 12B:
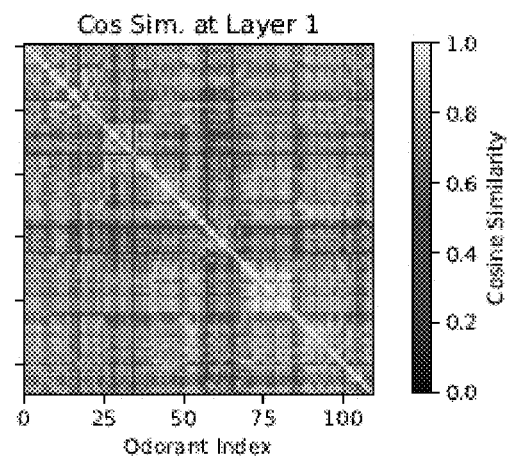
Figure 12C:
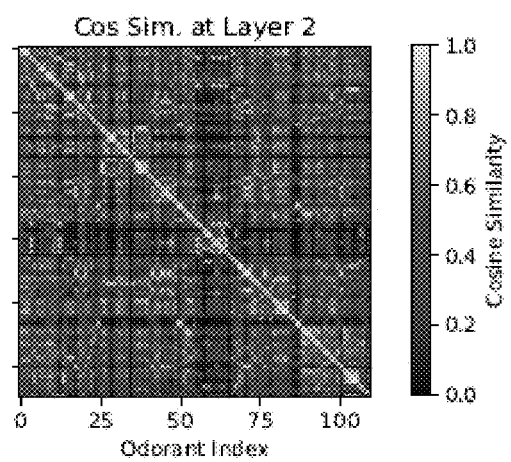
Figure 12D:
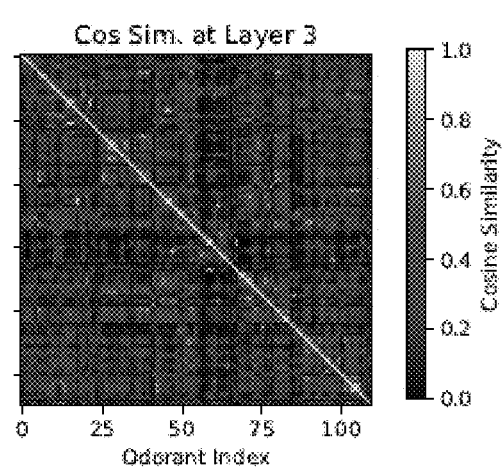
Figure 13A:
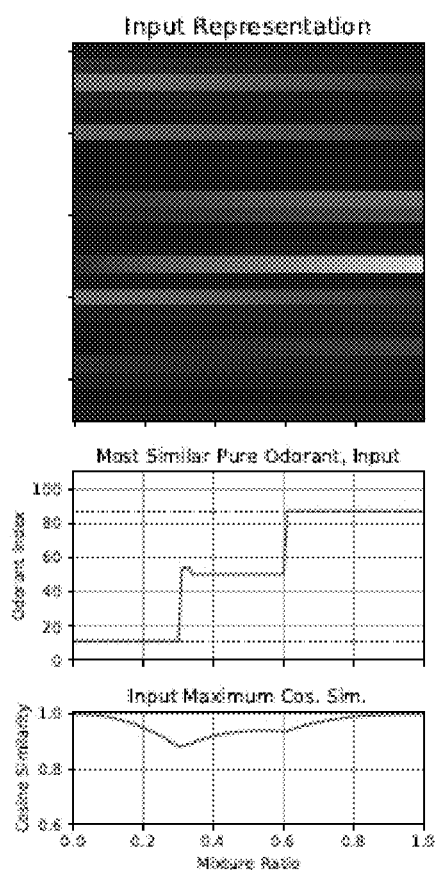
FIGS. 13A-13D show Mixture Classification based on output of different components in the OEM for input of the first circuit layer 110, the second circuit layer 120 and the third circuit layer 130, respectively. Top row corresponds to steady-state representation of odorant mixture at different layers of the OEM at various mixture ratios. Middle row shows the mono-molecular odorant most similar to the mixture for different layers at various mixture ratios. Two horizontal dashed lines indicate the mono-molecular odorants used to create the mixture. Bottom row shows the maximum Cosine Similarity between the mixture representation and all mono-molecular odorant representations at various OEM layers.
Figure 13B:
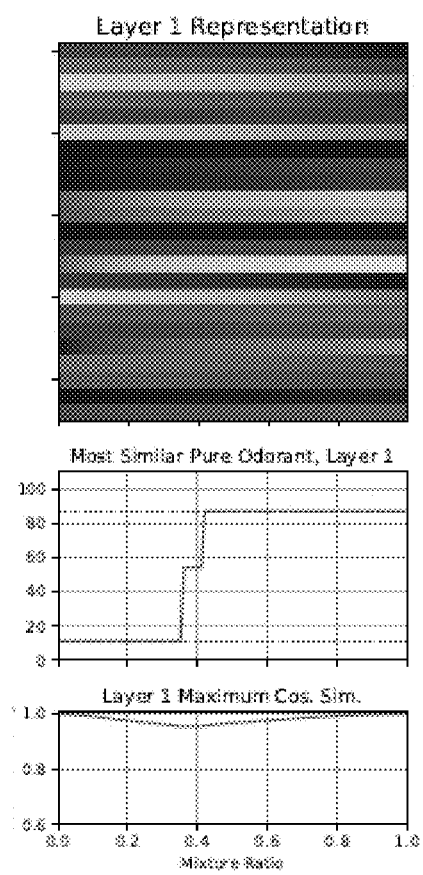
Figure 13C:
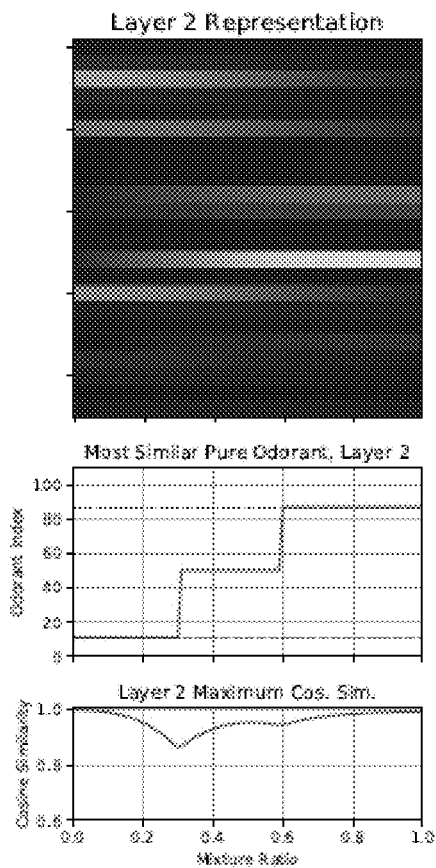
Figure 13D:
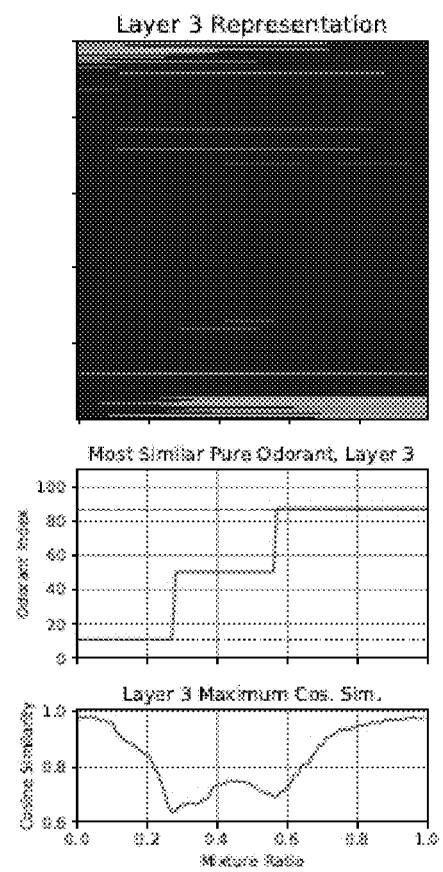

The present example provides examination of the second circuit layer 120. In this example, a mixture of two odorants, one background odorant with low concentration amplitude and one foreground odorant with five different concentration waveforms was tested, as shown in FIG. 10A. The output of the predictive coding circuit 124 can be visualized as heatmaps and traces as shown in FIG. 10B. When the concentration amplitude of the foreground was relatively larger than the background odorant (columns 2 to 5 in FIG. 10B), the predictive coding circuit 124 generated a robust combinatorial code for the foreground odorant between 2:5 and 4:5 seconds regardless of the shape of the concentration waveform. In certain embodiments, therefore, the OEM can process one or more mixtures of odorants represented as one or more shapes in a concentration waveform. The output of the on-off circuit 122 can be visualized as heatmaps and traces as shown in FIG. 10C. Two positive and one negative pulse can be observed. The first positive pulse indicates the onset of the background odorant. The second positive pulse and the negative pulse mark the onset and offset of the foreground odorants. The output of the second circuit layer 120 was visualized as heatmaps and traces as shown in FIG. 10D. For all 5 waveforms as shown in FIGS. 10A-10D there was a strong indication for the onset of the foreground at 2:5 seconds followed constant responses that recovers the odorant identity between 2:5 and 4:5 seconds. At 4:5 seconds, the output of the second circuit layer 120 was driven to zero by the on-off circuit 122 due to the offset of the foreground odorant.

Robust Real-Time Hash Code

The hash code generated at the output of the third circuit layer 130 was designed to: 1) represent the odorant identity in real-time, and 2) represent the odorant identity as a sparse code. As shown in FIGS. 11A-11D, the high-dimensional hash code generated by the third circuit layer 130 shows temporal dynamic that traces the onset and offset of both the foreground and background odorants. Moreover, across all channels of the feedback normalization circuit in the third circuit layer 130, a consistent 5-10% of the channels are active regardless of odorant identities and concentration waveforms in the input mixture. Such robust sparse hash code enables the OEM to classify not only mono-molecular odorants but also odorant mixtures.

Hash Code Sensitivity and Odorant Classification

To evaluate the performance of high-dimensional sparse hash code implemented by the Real-Time Hashing Circuit, its collision resistance was quantified by measuring the pair-wise distance between steady-state representations of various pure odorants. As shown in FIGS. 12A-12D, comparison of cosine similarity matrices between odorant representations at input and all stages of the processing circuit showed that each component in the OEM increasingly reduced similarity between odorant representations, thereby increasing collision resistance. Additionally, while the first circuit layer 110 and the second circuit layer 120 had collision resistance equivalent or worse than the input, the third circuit layer 130 drastically reduced similarity across odorant representations. As such, it appears that the third circuit layer 130 provides a hashing of odorants conducive to single odorant classifications as pure odorants are represented as disjoint hash codes.

The OEM can also allow classification of odorant mixtures, as it can separate the mixtures from known mono-molecular odorants used to preprogram the system. Particularly, when the cosine similarity between the OEM representation of the odorant mixture and all the other mono-molecular odorants is sufficiently low, and a classifier, acting on the output of the OEM, can distinguish the mixture from pure odorants.

To demonstrate the OEM's mixture classification capability, a pair of randomly selected monomolecular odorants were mixed via a convex combination of their corresponding binding vectors $\tilde{b}=(1-\alpha)\ b_1+\alpha \cdot b_2$, where $\alpha \in [0,1]$ is the mixture ratio between odorant 1 and 2. Driven by a shared constant concentration waveform $u_1(t)=u_2(t)=u$, the similarity between the steady-state representation of the odorant mixture and those of all mono-molecular odorants at different layers of the OEM was examined. The identity as well as the magnitude of the similarity of the pure odorant most similar to the mixture at different layers across mixture ratios was determined. As shown in FIGS. 13A-13D, across all layers of the OEM (as well as the input layer), monomolecular components of the odorant mixture are detected as the most similar odorant when the mixture ratio is biased to close to 0 or 1. Furthermore, at intermediate values of mixture ratios, all layers wrongly classify the mixture as another mono-molecular odorants. However, the maximum Cosine Similarity corresponding to the mis-classifications reveal that only at the third circuit layer 130 output is the classifier capable of detecting the error, since only at third circuit layer 130 does the maximum Cosine Similarity show a significant decrease across intermediate mixture ratios. Thus, the OEM including the third circuit layer 130 is capable of classifying odorant mixtures of a previously unseen input.

Although the presently disclosed subject matter and its advantages have been described in detail, it should be understood that various changes, substitutions and alterations can be made herein without departing from the spirit and scope of the disclosed subject matter. Moreover, the scope of the present application is not intended to be limited to the particular embodiments of the process, machine, manufacture, and composition of matter, methods and processes described in the specification.

As one of ordinary skill in the art will readily appreciate from the disclosed subject matter of the presently disclosed subject matter, processes, machines, manufacture, compositions of matter, methods, or procedures, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, methods, or procedures.

The invention claimed is:

1. An apparatus for identifying an odorant, comprising:
one or more circuit layers comprising one or more processors and including one or more olfactory sensors adapted to sense the odorant;
a memory, coupled to the one or more processors and storing instructions, which when executed cause the one or more processors to:
encode the sensed odorant;
determine an identity representation of the odorant based on the encoded sensed odorant; and
determine odorant information based on the identity representation of the odorant using a time-dependent hash code,
wherein the memory is further configured to cause the one or more processors to combine the identity of the odorant and the concentration waveform of the odorant as a combinatorial code of multidimensional spike trains.

2. The apparatus of claim 1, wherein the memory is further configured to cause the one or more processors to evaluate a distance of the identity representation of the odorant; and comparing the distance to other distances,
wherein the other distances represent a pair of previously identified odorants stored in the memory.

3. The apparatus of claim 2, wherein the distance is an absolute distance.

4. The apparatus of claim 1, wherein the odorant is a monomolecular odorant or an odorant mixture.

5. The apparatus of claim 1, wherein the memory is further configured to cause the one or more processors to classify the odorant information of a monomolecular odorant or an odorant mixture.

6. The apparatus of claim 1 further comprising a display, coupled to the one or more processors, and adapted to display the determined odorant information.

7. The apparatus of claim 6, wherein the memory is further configured to cause the one or more processors to display an indication of the odorant information.

8. The apparatus of claim 1, wherein the one or more circuit layers comprise:
a first circuit layer, a second circuit layer and a third circuit layer;
wherein the first circuit layer performs the encoding the sensed odorant to an electrical signal,
wherein the second circuit layer performs the determining an identity representation of the odorant based on the encoded electrical signal; and
wherein the third circuit layer performs determining odorant information using a time-dependent hash code based on the identity representation of the odorant.

9. The apparatus of claim 8, wherein the first circuit layer comprises an olfactory sensor array.

10. The apparatus of claim 9, wherein the sensors of the olfactory sensor array comprise asynchronous samplers.

11. The apparatus of claim 8, wherein the on-off circuit comprises at least one of a low pass-filter or a high pass filter.

12. The apparatus of claim 11, wherein the predictive coding circuit is configured to at least one of smooth, pool, and normalize the electrical signal.

13. A method for identifying an odorant, the method comprising:
sensing an odorant using an olfactory sensor;
encoding the sensed odorant using an input processor;
determining an identity representation of the odorant based on the encoded sensed odorant;

causing the one or more processors to combine the identity of the odorant and the concentration waveform of the odorant as a combinatorial code of multidimensional spike trains; and determining odorant information based on the identity representation of the odorant using a time-dependent hash code.

14. The method of claim 13, wherein the determining of the odorant information comprises:

evaluating a distance of the identity representation of the odorant; and comparing the distance to other distances, wherein the other distances represent a pair of previously identified odorants stored in the memory.

15. The method of claim 14, wherein the distance is an absolute distance.

16. The method of claim 13, wherein the odorant is a monomolecular odorant or an odorant mixture.

17. The method of claim 13, wherein the encoding comprises determining at least one of an identity of the odorant or a concentration waveform of the odorant.

18. The method of claim 13, wherein the identity representation is a concentration-invariant representation of the odorant.

* * * * *